(12) United States Patent
Manuelidis

(10) Patent No.: US 7,368,253 B1
(45) Date of Patent: May 6, 2008

(54) PRE-SYMPTOMATIC MARKERS FOR DISEASES ASSOCIATED WITH TRANSMISSIBLE SPONGIFORM ENCEPHALOPATHIES

(76) Inventor: Laura Manuelidis, 585 Ellsworth Ave., New Haven, CT (US) 06511

(*) Notice: Subject to any disclaimer, the term of this patent is extended or adjusted under 35 U.S.C. 154(b) by 69 days.

(21) Appl. No.: 11/073,180

(22) Filed: Mar. 4, 2005

Related U.S. Application Data

(60) Provisional application No. 60/572,457, filed on May 18, 2004, provisional application No. 60/550,633, filed on Mar. 4, 2004.

(51) Int. Cl.
G01N 33/567 (2006.01)
G01N 33/53 (2006.01)
G01N 33/542 (2006.01)
G01N 1/30 (2006.01)
H01L 21/20 (2006.01)

(52) U.S. Cl. .............. 435/7.21; 435/7.8; 435/7.92; 435/40.5; 436/501; 436/503; 436/504

(58) Field of Classification Search ............ None
See application file for complete search history.

(56) References Cited

OTHER PUBLICATIONS

J. Virology, 2002, 76, No. 21, pp. 10905-10913.*
Lin et al., 2001, J. Biol. Chem, vol. 276, No. 45, pp. 42077-42083.*
Ishida et al., 1994, J. Leukocyte Biol., vol. 54, pp. 797-806.*
Ferreira et al., 1999, J. Leukocyte Biol., vol. 66, 593-600.*
Hashimoto et al., Blood (2000) 96:2206-2214.
Manuelidis et al., Lancet (1985) 2:896-897.
Manuelidis et al., Science (1978) 200:1069-1071.
Internaional Search Report for PCT/US05/07189, mailed on Jan. 31, 2006, 2 pages.
Mabbott et al., J. Virology (2002) 76(10):5131-5139.
Starke et al., 43rd Annual Meeting of American Society of Hematology (2001) 98(11):247a-248a.
Arjona et al., PNAS USA (2004) 101:8768-8773.
Baker and Manuelidis, PNAS USA (2003) 100:675-679.
Baker et al., J. Neurovirol. (2004) 10:29-40.
Baker et al., J. Virol. (2002) 76:10905-10913.
Harrison et al., PNAS USA (1998) 95:10896-10901.
Lu et al., J. Cell. Biochem. (2004) 93:644-652.
Manuelidis and Lu, Neurosci. Lett. (2000) 293:163-166.
Manuelidis and Lu, PNAS USA (2003) 100:5360-5365.
Manuelidis et al., Science (1997) 277:94-98.
Manuelidis, Viral Immunol. (2003) 16:123-139.
Radebold et al., BMC Infectious Diseases (2001) 1:20.

* cited by examiner

*Primary Examiner*—Olga N. Chernyshev
(74) *Attorney, Agent, or Firm*—Morrison & Foerster LLP

(57) ABSTRACT

Markers for TSE that are present prior to formation of detectable pathological prion protein are useful to detect this infection prior to clinical signs. Additional markers are useful to detect the stage of TSE infection and distinguish it from other conditions which have similar clinical symptoms. Determinations on isolated cell preparations are particularly useful, especially those derived from peripheral (non-brain) sources.

6 Claims, 3 Drawing Sheets

(page 1 of 2)

(page 2 of 2)

PRE-SYMPTOMATIC MARKERS FOR DISEASES ASSOCIATED WITH TRANSMISSIBLE SPONGIFORM ENCEPHALOPATHIES

CROSS-REFERENCE TO RELATED APPLICATIONS

This application claims benefit under 35 U.S.C. § 119(e) of provisional application Ser. Nos. 60/572,457 filed 18 May 2004 and 60/550,633 filed 4 Mar. 2004. The contents of these documents are incorporated herein by reference.

STATEMENT OF RIGHTS TO INVENTIONS MADE UNDER FEDERALLY SPONSORED RESEARCH

This invention was made with support from National Institutes of Health and the Department of Defense. The U.S. government has certain rights in this invention.

TECHNICAL FIELD

The invention relates to methods to assess the presence of infection that affect the brain and can be associated with abnormal amyloid components, such as Creutzfeldt-Jakob disease (CJD), bovine spongiform encephalopathy (BSE), scrapie, and other related diseases associated with host-encoded prion protein (PrP) amyloid and to distinguish them from other such conditions that are not the result of infection, such as Alzheimer's. More specifically, the invention provides markers for the conditions that may be assessed prior to symptoms previously recognized.

BACKGROUND ART

There are a number of infectious diseases in mammalian subjects that appear to be associated with mis-folded forms of native protein—i.e., are characterized by high levels of normal and abnormal prion protein (PrP). Among these are bovine spongiform encephalopathy (BSE) in bovine subjects, scrapie in sheep, Chronic Wasting Disease (CWD) in ungulates, and Creutzfeldt-Jakob disease (CJD) in humans. Collectively, these conditions are called transmissible spongiform encephalopathies (TSE's) and this terminology will be used in the present application.

The infectious agent for these conditions has not been identified, but it is known that the infection can be transmitted through the food supply as well as through peripheral routes including white blood cells in experimental animals and in humans. Manuelidis, E. E., et al., *Science* (1978) 200:1069-1071; Manuelidis, E. E., et al., *Lancet* (1985) 2:896-897. Two strains of CJD have been identified—an attenuated SY strain and a more virulent FU strain. Manuelidis, L., et al., *Proc. Natl. Acad. Sci. USA* (2003) 100: 5360-5365. The ability of the SY strain to protect against infection by the FU strain was ascribed to a successful immune response (ibid.). It has been shown that the infectious particle for CJD has a viral size of about 25 nm and infectivity is markedly reduced by conditions that disrupt viral core components. Manuelidis, L., *Viral Immunol.* (2003) 16:123-139. Myeloid cells are believed to play a significant role in the spread of infection (ibid.). Long nucleic acids have also been identified in some high titer preparations of the infectious strain (ibid.). See also Manuelidis, L., et al., *Neurosci. Lett.* (2000) 293:163-166.

The effect of FU and SY strains in neuronal cell lines with differing patters of PrP resistant to proteolysis (PrP-res) was also studied by Arjona, A., et al., *Proc. Natl. Acad. Sci. USA* (2004) 101:8768-8773. It has also been shown that CJD is transferred from brain via the blood to the gut at early stages of infection. Radebold, K., et al., *BMC Infectious Diseases* (2001) 1:20. Other animals besides humans, sheep and cattle have also been affected by the same or analogous agents, including pigs, rodents, primates, cats, and various zoo animals. See, for example, Manuelidis, L., et al., *Science* (1997) 277:94-98.

Earlier work by the present applicants has shown that certain genes are highly expressed in microglia comprised of a specialized type of brain myeloid cells isolated from CJD infected brains. Baker, C. A., et al., *J. Virol.* (2002) 76:10905-10913 and Baker, C. A., et al., *Proc. Natl. Acad. Sci. USA* (2003) 100:675-679 isolated microglia cells from the brains of both normal mice and mice infected with a strain of CJD about 130 days after inoculation (after symptoms appear) and determined comparative levels of gene expression using mRNA isolated from the samples and gene microarray technology. It was found that mRNA's involved in inflammatory functions were substantially increased by 5-20 fold in CJD microglia; these included IL1 molecules responsible for macrophage respiratory bursts (gp91phox and p22phox) and several other leukocyte surface molecules, as well as complement cascade components C1q, properdin, and factor H. Also elevated was the complement receptor subunit CD18, lipoprotein lipase, CD36, and CD68. Also elevated was serum amyloid A3 (SAA3) and molecules associated with interferon signaling. The most potently induced transcript was lysozyme M. Extensive profiles were provided in both articles and compared to profiles of expression obtained when normal cells were stimulated with lipopolysaccharide to mimic bacterial infection or by interferon γ to mimic inflammation. Alterations were found in the profiles of normal cells thus stimulated, but these profiles did not replicate those obtained from cells isolated from rodents that had been inoculated with CJD and exhibited symptoms of this condition. Similarly, treating normal cells with prion protein resistant to proteolysis (PrP-res) did not appear to produce the type of changes in expression levels shown in cells derived from CJD inoculated animals.

More recently, Baker, C. A., et al., *J Neurovirol.* (2004) 10:29-40 further investigated certain interferon-sensitive transcripts as upregulated in brain and in cells of the microglia obtained as soon as 10 days after inoculation. Additional studies of early markers were reported by Lu, Z. Y., et al., *J. Cell. Biochem.* (2004) 93:644-652.

In addition, Harrison, J. K., et al., *Proc. Natl. Acad. Sci. USA* (1998) 95:10896-10901 showed that elevated levels of CX3CR1 is associated with mediation of microglial-neuronal interactions; Hashimoto, S. I., et al., *Blood* (2000) 96:2206-2214 showed that the protease inhibitor cystatin F is specifically expressed in human activated and mature dendritic cells.

It is known that abnormal PrP is formed in the brain about 90 days after infection, i.e., experimental inoculation with rodent-passed CJD or similar CJD strains. Thus, at the time the markers enumerated above were determined, the abnormal PrP presence in the brain was well established. The markers described in the present invention are present at detectable levels before the appearance of abnormal PrP. Furthermore, the markers appear not only in the microglia, but also in the peripheral system, including blood, gut, urine and the like, and in cells isolated from these sources. Thus, these markers provide a convenient early warning assay for TSE infection prior to the appearance of alternative symptomologies, including the appearance of PrP in the microglia. Because these markers are present in the peripheral system, the assessment can be made on accessible body fluids and cells. Further, because some of the markers are different from those in Alzheimer's disease brain, they can be used to distinguish TSE infection from Alzheimer's in symptomatic patients. In addition, use of the markers may distinguish various TSE strains.

DISCLOSURE OF THE INVENTION

The invention provides markers for diagnosis of early stage TSE infection, for distinguishing TSE from Alzheimer's, and for identifying TSE strains. The markers can be assessed in the brain or in the peripheral system and in isolated cell preparations and can determine the presence of TSE infection prior even to the formation of abnormal prion protein (PrP). The pattern of markers is also indicative of the stage of infection.

Thus, in one aspect, the invention is directed to a method to identify a subject that has been infected with a transmissible spongiform encephalopathy (TSE) which method comprises determining, in at least one sample, e.g., body fluid or isolated cell preparation of said subject, the level of a marker associated with early response to infection and comparing the level to that characteristic of a corresponding sample from a normal subject. A difference in level of the marker as compared to the level in normal samples identifies the subject as infected. Multiple markers and patterns of marking can also be determined. Suitable early markers include, for example, serum amyloid A3 (SAA3), L-selectin, MIP-1α, MIP-1β, MCP, IL-1β, TNFα, and Toll-like receptor (TLR)4. Early detection of infection can also be demonstrated using elevated levels of CD72, CD84, LY86, CXCL13, IFI204, LY9, IFI202, ImmResG1, CXCL10, RSG15, PRF7, RANTES and OAS as indicators. The level of GAPDH may be used as a control. All of these genes provide distinct levels of mRNA and protein prior to formation of detectable levels of PrP. In addition to the markers discussed above, additional genes are expressed at different levels depending on the nature of the sample assessed.

In one embodiment of the invention, the expression levels of markers are determined in isolated cell types which appear to provide clear information as to the levels of the indicators. In addition, individual cell types may be stimulated by treating with specific chemicals and inducers to accentuate differences in cells obtained from subjects exposed to TSE versus normal controls. Cells obtained from TSE inoculated subjects appear to display accentuated differences in levels of expression of many of the marker genes when treated with general immune stimulants such as double-stranded RNA or other agents which interact with the Toll-like receptors. Additional markers to those set forth above where cells from TSE stimulated subjects showed levels of markers at least 2.5-fold different from levels in normal cells (both increased and reduced levels are included) are shown in Table 2 (for isolated astrocytes), Table 3 (for B cells) and Table 4 (for myeloid cells). It is not to be implied that these markers are characteristic only of the cells for which results are illustrated. They are useful in other cell types as well.

In particular, one embodiment of the invention relates to determining levels of indicator genes in cell types from tissues and fluids peripheral to the central nervous system (CNS).

In another aspect, the invention is directed to a method to distinguish TSE infection from Alzheimer's, which method comprises determining levels of markers characteristic of TSE, but not associated with Alzheimer's.

In still another aspect, the invention is directed to discriminating among various stages of the disease by assessing the levels of these markers as a function of time.

BRIEF DESCRIPTION OF THE DRAWINGS

FIGS. 1C-1D also demonstrate the enhancing effect of treating assessed microglia cells with poly I:C.

MODES OF CARRYING OUT THE INVENTION

Figure 1:
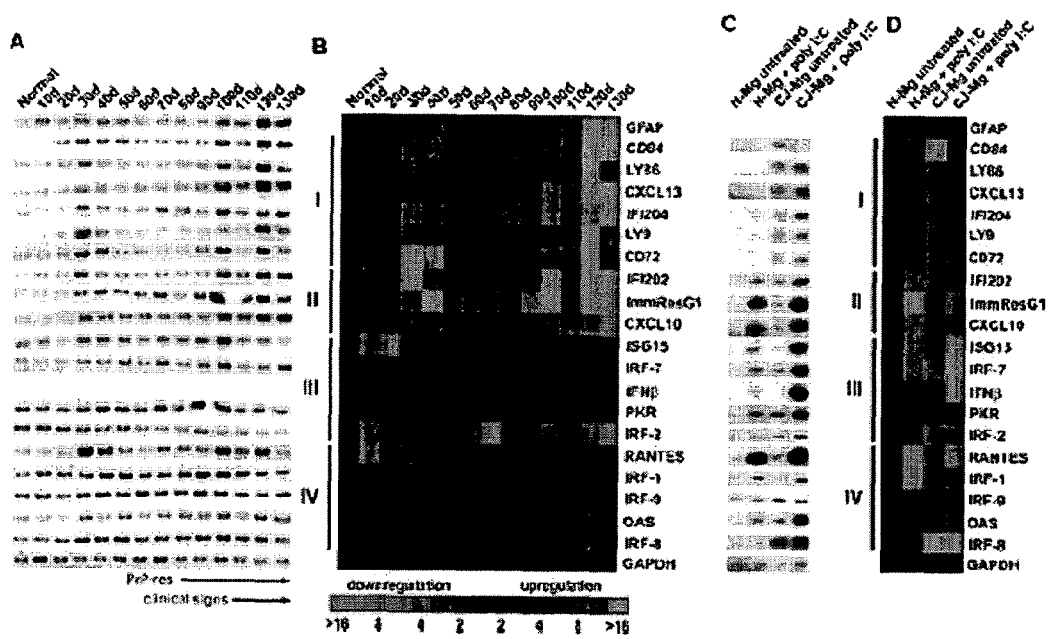
FIGS. 1A-1D show the level of marker mRNA in brain and microglia as determined by RT-PCR as a function of time.

The invention provides markers for TSE which are detectable and measurable prior even to the appearance of pathologic prion protein.

The assays can be conducted on tissue such as brain, gut or spleen tissue from a subject but most conveniently from biological fluids of the subject, such as cerebrospinal fluid, blood or its components, urine, lymphatic fluid, saliva or even contents of the gastric system. The subject is generally a mammalian subject; as noted above, TSE conditions are found in zoo animals, cats, sheep, cattle, and humans and other primates. Convenient fluids for assay include plasma and serum prepared as generally understood for diagnostic tests.

In one embodiment, the assays are conducted on isolated cell types such as microglia, astrocytes, and various cells associated with the spleen such as B cells, T cells and myeloid cells. Thus, the samples useful for assessment of the level of gene expression either at the mRNA level or the protein level, include tissue samples which comprise heterogeneous cell types, fluids which may themselves contain cells, and "isolated cell preparations" which are relatively homogeneous as to cell type. "Isolated cell preparations" contain at least 80%, 85%, 90%, 95% or more than 95% cells of the same differentiated form and tissue origin, such as myeloid cells from the microglia, myeloid cells from the spleen, B cells from the spleen, B cells from plasma, and the like. Cells derived from tissues and fluids peripheral to the CNS are particularly convenient.

The information obtained by assessing gene expression is evaluated by comparing these levels in the sample to be tested with the levels found in a corresponding normal sample. By "corresponding normal sample" is meant a sample prepared in substantially the same manner as that tested but from one or more individuals known not to be infected with a TSE agent. The data with regard to normal levels may be obtained simultaneously using one or more corresponding normal samples as a control or, preferably, data obtained from normal samples can be stored and retrieved for comparison with the test results. Levels in a "corresponding normal sample" thus is construed to refer to data associated with such samples however obtained and stored.

The markers can be assessed by a variety of methods, either by determining the level of messenger RNA transcribed by the expressed gene or by determining the level of protein produced or both. Typically, the level of mRNA or protein detectable in the sample will differ at least two-fold, or three-fold or five-fold, 10-fold, 20-fold or 40-fold from that in a corresponding normal sample. As has been found by the present inventors, the expression levels of the markers described herein are variable over the time period post inoculation and thus, depending on the nature of the markers chosen, and if applicable, the nature of the pattern obtained, the stage of progression of the TSE infection can be evaluated. In the case of isolated cell types, for example, the levels of the markers assessed may increase or decrease and the levels in cells from TSE inoculated subjects are at least 2.5-fold higher or lower than those in normal cells. As noted above, it may be useful to assess the level of more than one marker in evaluating the stage of the condition. Simply to identify an infected subject, it is preferred that early stage markers be employed since there are no other indicators available for this condition. At later stages, markers may be useful to distinguish TSE infection from other conditions which affect the brain, such as Alzheimer's disease. Since the markers assessed herein are associated with response to infection, elevated levels of these markers in either early or late stage are not found in Alzheimer's subjects.

In order to make a complete assessment, it may also be useful to obtain expression levels and/or patterns from a variety of sample types, such as B cells as well as astrocytes. Practitioners can readily design protocols which provide the maximum amount of diagnostic information in the most efficient manner by selecting those markers appropriate to the diagnostic purpose. Assessment of multiple markers in only a single sample type or in multiple sample types may also be employed. It may be advantageous to utilize markers that have different characteristics. For example, it appears that the patterns exhibited by markers such as GFAP, CD84, LY86, CXCL13, IFI204, LY9, and CD72 are similar and are biphasic in nature; weaker biphasic patterns (bridging both early and late stages of infection) are exhibited by ISG15, IRF7, IFN-β, PKR and IRF2. Fairly consistent increases in levels of expression as the condition progresses is exhibited by IFI202, ImmResG1, and CXCL10.

In one embodiment, especially if only a single early marker is used, the marker is other than GFAP, CD84, LY86, CXCL13, IFI204, LY9, CD72, ISG15, IRF7, IFNβ, PKR, IRF2, IFI202, ImmResG1, or CXCL10.

As defined herein, "early stage" or "early markers" refer to those whose levels are altered prior to 50 days subsequent to infection. "Middle stage markers" are those where levels differ from those in normal samples between 50 and 80 days. "Late stage markers" or "late markers" are those that are altered as compared to normal tissue during the period subsequent to 80 days after initial infection. Some markers appear at all stages of infection and thus identification of a marker as an "early stage" marker does not necessarily mean that it is not present in another stage of infection as well. Typically, clinical signs of infection appear only about 110 days subsequent to infection whereas the presence of PrP-res occurs around 90 days after inoculation.

For assessing mRNA levels, a variety of methods is known, including Northern blot probed with an oligonucleotide which hybridizes under stringent conditions to the mRNA to be detected, use of quantitative PCR employing appropriate primers, use of other amplification techniques or by microarrays. Levels can be assessed using standard gene chip technology or other art-known methods.

Although the examples below employ murine systems, counterparts in other species are available in the art due to sequencing efforts, e.g., the human genome sequencing project. The primers described in the examples are derived from murine systems; however, the same homologous human genes may be found on the NCBI database or in GenBank and the relevant sequence can be used to design primers useful for human samples. Databases for other species are also available.

For detection of the protein, typically immunoassays are often employed although any specific binding assay for the protein, such as use of a receptor for detecting a ligand or vice versa could also be used. In addition to whole antibodies, fragments and modified forms that are immunospecific can be used as the detection reagent with suitable labels such as radioactive labels, fluorescent labels, enzyme labels and the like. A wide variety of formats for immunoassays is known in the art and need not be repeated here. Microarrays designed to detect proteins are also available, and two-dimensional chromatography could also be employed. Flow cytometric techniques can also be used.

Expression products of the genes that are upregulated include expression products of serum amyloid A3 (SAA3), and L-selectin as well as MIP-1α, MIP-1β, MCP1, IL-1β, TNFα, IFI202, IFI204, CD72, LY9, CXCL10, and CX3CR1 and others as noted in the examples below. Suitable oligonucleotides, PCR primers, and antibodies are either available in the art or can readily be prepared for these known expression products. The examples provide experimental evidence of altered levels of markers associated with various stages of the infection and thus various combinations and sub-combinations of these markers can conveniently be used as the basis for assay. Those of skill in the art will readily determine convenient individual assays or combination. As an illustration only, in order to detect the presence of infection in a subject that shows no clinical symptoms, appropriate markers include SAA3, CD84, cathepsin S., or any of the markers shown in Table 1 below as indicative of early stage infection and combinations thereof. MIP-1α is also a convenient marker; it is present in late stage as well but because it is present in the early period, it can be used to detect the presence of infection of subjects who show no symptomology.

Elevated levels of CXCL13 are present at high levels in late stage infection but not early stage infection, and thus would be expected to correlate with clinical symptoms and to distinguish the presence of TSE infection from alternative diagnoses such as Alzheimer's. Data obtained from microglia related to levels of gene expression illustrated in Table 1 for microglial derived samples might then conveniently be combined with data with regard to, for example, CD24a which has an altered level in astrocytes.

The following examples are offered to illustrate but not to limit the invention.

EXAMPLE 1

Determination of Upregulated Genes

CD-1 mice were intracerebrally inoculated with 30 μl of a 1% brain homogenate containing the FU (fast acting) strain of the CJD agent. In parallel, animals were inoculated with normal brain homogenate to control for nonspecific effects of intracerebral inoculation. At 10 day intervals, RNA was isolated from total brains by homogenization in TRIzol® (Invitrogen, Carlsbad, Calif.). Microglia (95% CD 11b$^+$ cells) were isolated from the brains of mice with clinical signs of CJD or age-matched controls using previously established protocols (Baker, et al. (2002)). Cells were maintained in vitro for 16-18 hours at 37° and 5% $CO_2$ in microglial medium (RPMI-1640 with 5% fetal bovine serum, 10 mM HEPES, 1 mM sodium pyruvate, 50 units/ml penicillin, 50 μg/ml streptomycin). Following this brief culture period, cultures were quickly rinsed with microglial medium to remove any remaining debris before RNA extraction with TRIzol®. For stimulation of the TLR9 receptor (Dalpke, et al., *J. Immunol.* (2002) 168:4854-4863), unmethylated CpG DNA oligonucleotides (TCCATGACGTTC-CTGATGCT) (SEQ ID NO.:47) or oligonucleotides with an inverted CpG motif (TCCATGAGCTTCCTGATGCT) (SEQ ID NO.:48) were included in the overnight culture at a final concentration of 3 μM.

Digestion of RNA samples with DNAse I, reverse transcription, and PCR amplification with biotinylated nucleotides were performed as described by Baker, C. A., et al., *J. Virol.* (2002) 76:10905-10913. The number of PCR cycles required for detection within the linear range of amplification was determined empirically for each product. These optimal PCR conditions and primer sequences are listed below.

| Gene | Anneal (° C.) | No. cycles | Forward Primer | SEQ ID NO: | Reverse Primer | SEQ ID NO: |
|---|---|---|---|---|---|---|
| C1qα | 65 | 21 | GGACAGCGGCCCCCAAGGACT | 1 | CAGGCCGAGGGGAAAATGAGGAATC | 2 |
| C1qβ | 65 | 22 | CTACGGGGCTACACAGAAAGTCG | 3 | CAGGGAAAAGCAGAAAGCCAGTGAAGA | 4 |
| Cathepsin D | 60 | 19 | GGCAACCCGGAGGAGAACTAA | 5 | CCACTGGGAGGGGTATGTC | 6 |
| Cathepsin L | 65 | 20 | CAGGGCCAGTGCGGGTCTTGT | 7 | GTTGTCCCGGTCTTTGGCTATTTTGATGTA | 8 |
| CD14 | 59 | 25 | CTTCCTCAGATCCGAAGCCAGATTG | 9 | TCGCCCAATTCAGGATTGTCAG | 10 |
| CD48 | 63 | 26 | ACCACCGGCAGCAATGTAACCCTG | 11 | GTCGTTCTTGCTGCTTACAGGATTGC | 12 |
| CD68 | 60 | 26 | CAACAAAACCAAGGTCCAGGGA | 13 | CCAATGATGAGAGGCAGCAAGA | 14 |
| CX3CR1 | 60 | 24 | AGCTGCTCAGGACCTCACCAT | 15 | GTCATATGCAGGAACTCTGGG | 16 |
| Cystatin F | 65 | 28 | CAGCCATGTGGCTGGCCATTCTGCTTG | 17 | ACTTCAGAGTAGCAATATAGAGTCCGC | 18 |
| GAPDH | 60 | 20 | GACCTCAACTACATGGTCTACAT | 19 | TGGTTCACACCCATCACAAACAT | 20 |
| IL-1β | 63 | 29 | TGCAAGTGTCTGAAGCAGCTATGG | 21 | GGTGGGTGTGCCGTCTTTCATTACA | 22 |
| L-selectin | 65 | 31 | ACTCTGGGAAATGGAACGATGAC | 23 | AATGAAGAGGGGGTTGTAGTCACC | 24 |
| Mac2 | 72 | 26 | TATCCTGCTGCTGGCCCTTATGGTGTCC | 25 | CGTGGTTAGCGCTGGTGAGGGTTATGTC | 26 |
| MCP1 | 60 | 28 | CCACTCACCTGCTGCTACTCATTC | 27 | GTCACTCCTACAGAAGTGCTTGAGG | 28 |
| MIP-1α | 60 | 28 | GAAGAGTCCCTCGATGTGGCTA | 29 | CCCTTTTCTGTTCTGCTGACAAG | 30 |
| MIP-1β | 60 | 32 | CCACAATAGCAGAGAACAGCAAT | 31 | AACCCCGAGCAACACCATGAAG | 32 |
| Properdin | 72 | 25 | AGAGACATCAGGGTAGAAGACTGCTG | 33 | ATAGGCTGGTCCTGAGCAGGGTTTC | 34 |
| SAA3 | 67 | 34 | ATGAAGCCTTCCATTGCCATCATTC | 35 | TCAGTATCTTTTAGGCAGGCCAGC | 36 |
| TLR2 | 68 | 25 | ACAGTAGAGAACAGCAAGGTCTTCC | 37 | GCTCTTGCAGCCGAGGCAAGAAC | 38 |
| TLR3 | 65 | 28 | GCAGTTTCCAACTCTGGATCTACC | 39 | GTGTTTGCAAAGACATTTGAAAGGGTG | 40 |
| TLR4 | 68 | 25 | TCGTTCAGTGAGCTACCACAGTTGC | 41 | TGCCATTAGGCAGGGTGCCATTGG | 42 |

-continued

| Gene | Anneal (° C.) | No. cycles | Forward Primer | SEQ ID NO: | Reverse Primer | SEQ ID NO: |
|---|---|---|---|---|---|---|
| TLR9 | 68 | 31 | TTTCTCTTGGTTAGG CCAACTCAGG | 43 | ACTGGGATTTCATCTA AGCCGTTGG | 44 |
| TNFα | 60 | 32 | GCTGGAAGACTCCTC CCAGGTA | 45 | ATGATCCGCGACGTGG AACTG | 46 |

PCR products were separated on agarose gels, transferred to Biodyne® B nylon membranes (Pierce, Rockford, Ill.), then visualized with the BrightStar® BioDetect™ kit (Ambion, Austin, Tex.) and BioMaX™ MR film (Kodak, New Haven, Conn.). Densitometry was conducted using National Institutes of Health (NIH) Image, with normalization to glyderaldehyde-3-phosphate dehydrogenase (GAPDH) to control for differences in starting RNA quantity. Results were expressed in terms of fold change relative to normal brain.

Figure 2:
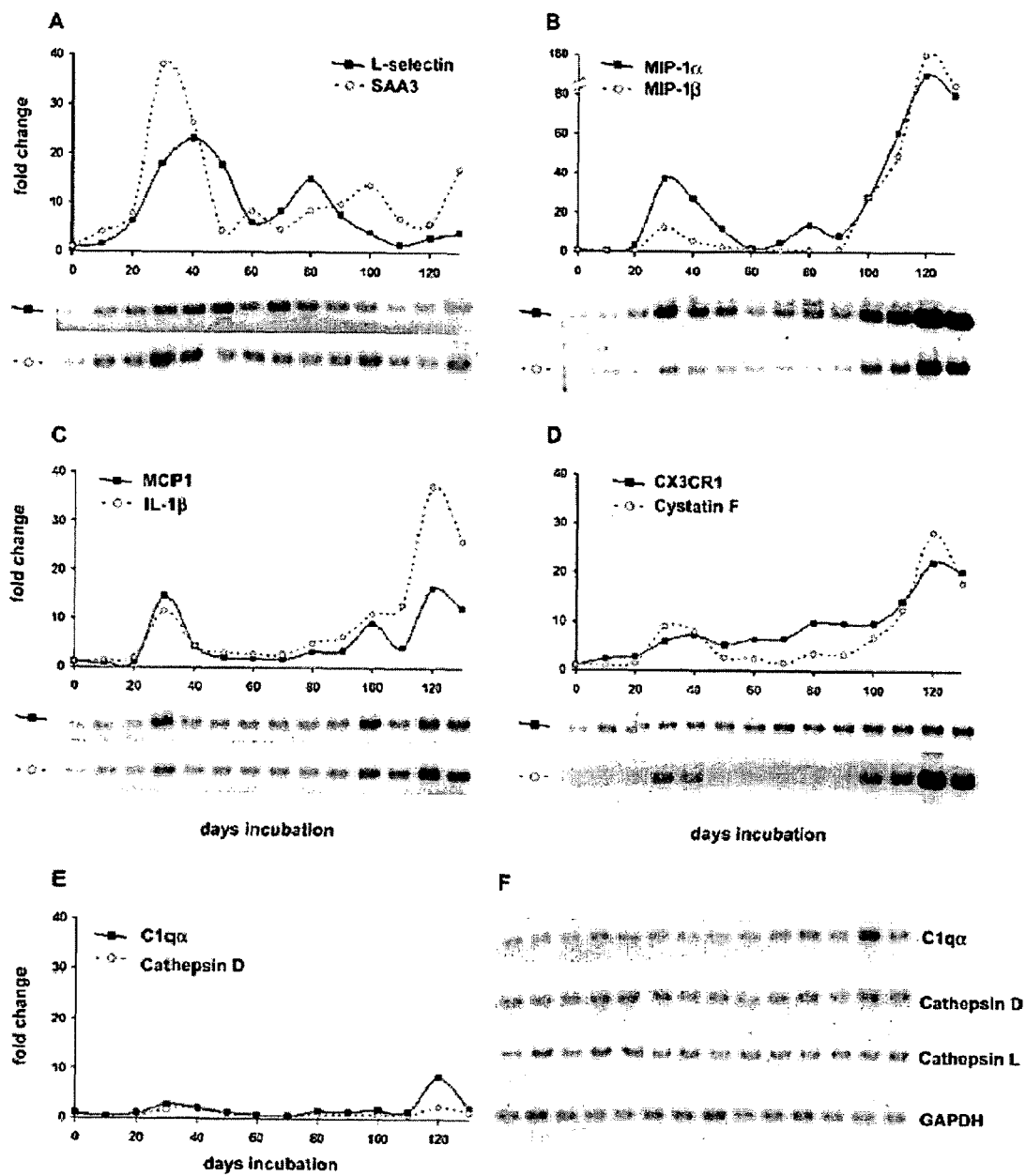
FIGS. 2A-2I show a graphical representation of the time course of expression in microglia for various genes in TSE infection.
Figure 2:
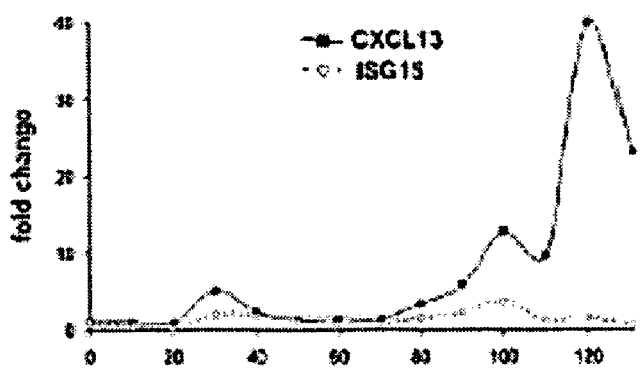
Figure 2:
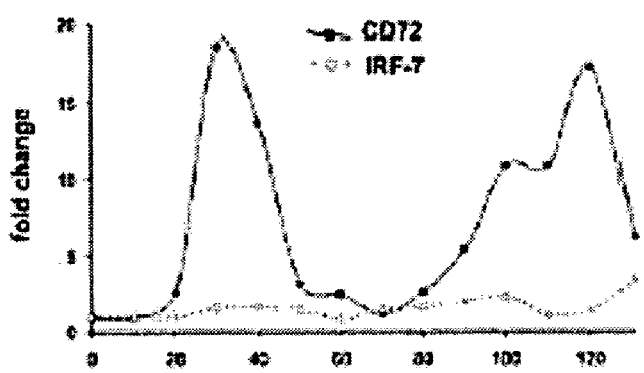
Figure 2:
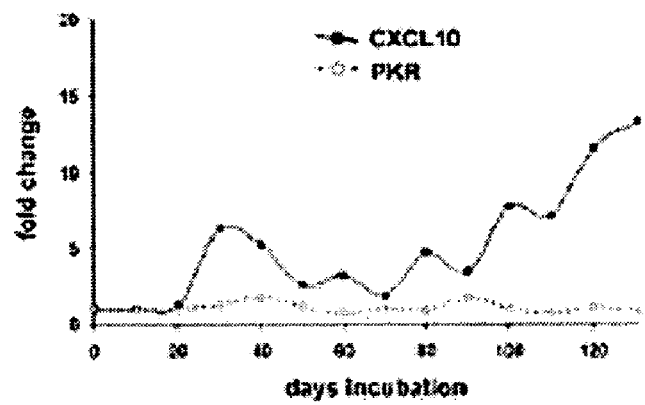

FIGS. 1A-1D show levels of upregulation of certain inflammation-linked transcripts in mouse CJD brain or microglia at early timepoints after inoculation. FIGS. 1A and 1B show the results from brain tissue; FIGS. 1C and 1D show the results obtained from samples more than 95% pure in microglial cells. These panels also include results when poly I:C is employed. FIG. 2 shows the results graphically for some markers. These alterations occurred long before any PrP-res or clinical disease signs, and often persisted throughout the course of disease. L-selectin and serum amyloid A3 (SAA3) exhibited some of the earliest changes, with induction occurring as soon as 10-20 days after inoculation. These increases coincide with significant reproduction of the infectious agent, which begins at 20 days in experimental CJD (Manuelidis, L., et al., *Virology* (1996) 216:46-59). Normal brains did not show upregulation of these transcripts. The temporal expression pattern of these two transcripts was unlike that of any other genes examined, because upregulation was higher at these early times than at later stages of disease. Peak levels of SAA3 occurred at 30 days and subsided by 50 days, whereas L-selectin levels reached their peak at 40 days and decreased somewhat thereafter. These declines were not secondary to neurodegeneration, because pathological changes in the brain begin only after 90 days.

Flow cytometry analysis of leukocytes from CJD brain revealed no increase in cells positive for both cell-surface L-selectin and the T cell marker CD3, which demonstrates that upregulation of L-selectin mRNA reflects a response of resident glial cells to CJD infection, and is not due to transient influx of T lymphocytes positive for L-selectin.

At 30 days after inoculation, the myeloid cell recruitment factors MIP-1α, MIP-1β, and MCP1 were induced, as well as IL-1β and TNFα proinflammatory activators. Each of these was upregulated at least tenfold and then decreased somewhat prior to massive upregulation of 20-100 fold during neurodegenerative stages of disease. The temporal profile of these genes was therefore distinct from the pattern of L-selectin and SAA3.

Significant levels of mRNA's for CX3CR1 and cystatin F were seen as early as 30 days after inoculation, with peak increases of >20-fold at the terminal stage of disease. Little or no response to CJD infection was shown by the complement cascade components C1qα and C1qβ or by cathepsin D and cathepsin L.

The Toll-like receptor (TLR) family of proteins involved in host recognition of viruses and other pathogens was also evaluated. Microglia treated with particular TLR agonists exhibit transcriptional changes that partially overlap with those observed in microglia isolated from CJD brain, and peripherally inoculated scrapie can be retarded by injection of unmethylated CpG oligonucleotides known to bind TLR9, Sethi, S., et al., *Lancet* (2002) 360:229-230.

Although TLR9 mRNA was detectable in spleen cells by RT-PCR, no transcripts could be detected in whole brain or adult microglia using this sensitive assay. Transcripts for TLR2 and TLR3 were detected in brain, but they remained unchanged over the course of CJD infection, but TLR4 mRNA levels showed 10-fold increases at 40 days and 15-fold at 90 days.

EXAMPLE 2

Levels of TSE Markers as a Function of Time

As described in Example 1, levels of various markers were determined in the brain of the mouse CJD brain at various time points. The results are shown in Table 1 below.

TABLE 1

| | Days | | | | | | | | | | | | |
|---|---|---|---|---|---|---|---|---|---|---|---|---|---|
| | 10 | 20 | 30 | 40 | 50 | 60 | 70 | 80 | 90 | 100 | 110 | 120 | 130 |
| SAA3 | + | + | +++ | +++ | + | + | + | + | + | ++ | + | + | ++ |
| L-selectin | − | + | ++ | ++ | ++ | + | + | ++ | + | + | − | − | + |
| MIP-1α | − | − | +++ | +++ | ++ | − | + | ++ | + | +++ | ++++ | ++++ | ++++ |
| ImmResG1 | − | − | ++ | ++ | + | + | + | + | ++ | ++ | ++ | +++ | ++ |
| MIP-1β | − | − | ++ | + | − | − | − | − | − | +++ | +++ | ++++ | ++++ |
| IFI202 | − | − | ++ | + | + | − | − | + | + | ++ | ++ | ++ | +++ |
| IFI204 | − | − | ++ | + | − | − | − | + | + | ++ | + | ++ | ++ |

TABLE 1-continued

| | Days | | | | | | | | | | | | |
|---|---|---|---|---|---|---|---|---|---|---|---|---|---|
| | 10 | 20 | 30 | 40 | 50 | 60 | 70 | 80 | 90 | 100 | 110 | 120 | 130 |
| CD84 | − | − | ++ | ++ | + | − | − | + | + | + | + | ++ | ++ |
| CD72 | − | − | ++ | ++ | − | − | − | − | + | ++ | + | ++ | + |
| IL-1β | − | − | ++ | + | − | − | − | + | + | ++ | ++ | +++ | +++ |
| MCP1 | − | − | ++ | + | − | − | − | − | − | + | + | ++ | ++ |
| LY9 | − | − | ++ | + | − | − | − | − | − | − | − | ++ | + |
| TNFα | − | − | ++ | − | + | − | − | ++ | ++ | ++ | ++ | ++++ | +++ |
| CX3CR1 | − | − | + | + | + | + | + | + | + | + | ++ | ++ | ++ |
| Cathepsin S | − | − | + | ++ | + | − | − | + | + | + | + | ++ | ++ |
| CD68 | − | − | + | + | − | − | − | − | + | ++ | − | ++ | + |
| Cystatin F | − | − | + | + | − | − | − | − | − | + | ++ | +++ | ++ |
| CXCL13 (BLC) | − | − | + | − | − | − | − | − | + | ++ | ++ | +++ | +++ |
| LY86 (MD-1) | − | − | + | − | − | − | − | − | − | + | + | +++ | ++ |
| CXCL10 (IP-10) | − | − | + | + | − | − | − | + | − | + | + | ++ | ++ |
| RANTES | − | − | + | + | − | − | − | − | − | + | − | + | − |
| C1qα | − | − | − | − | − | − | − | − | − | − | − | + | − |
| PrP-res | − | − | − | − | − | − | − | − | + | ++ | ++ | +++ | +++ |
| Clinical Signs | − | − | − | − | − | − | − | − | − | − | + | ++ | +++ |
| | Early | | | | Middle | | | | | Late | | | |

− = no significant change; + = greater than 4-fold change; ++ = greater than 10-fold change; +++ = greater than 25-fold change; ++++ = greater than 50-fold change.
PrP-res and clinical signs indicate subtle (+) to maximal (+++).

As shown in Table 1, early markers of the condition that appear prior to even 50 days subsequent to inoculation include L-selectin, SAA3, IFI202, TNFα, MIP-1α, MIP-1β, IFI204, ImmResG1, CD84, CD72, LY9, IL-1β, and MCP1. Low levels of CXCL10, CX3CR1, CXCL13, LY86, Cystatin F and RANTES also appear early. Detectable levels of some of these are maintained in a middle phase between 50 and 80 days.

Late phase markers which do not appear until subsequent to the 90 day timeframe required for appearance of the PrP-res include C1qα and CD88. Levels of CXCL10 and CX3CR1 are increased as the disease progresses.

Thus, it is possible to diagnose the stage of the disease by evaluating the appropriate marker. For example, samples which showed the strong presence of L-selectin, SAA3, or a number of other markers shown in Table 1 but are devoid of C1qα and CD88 indicate an early phase of the disease, while the absence of L-selectin but the presence of C1qα or DD88 indicates a later stage of this condition.

EXAMPLE 3

Determination of Markers in Isolated Cell Types

Astrocytes were purified from normal and late-stage CJD-infected brain by centrifugation, MACS columns, and in vitro culture to obtain purities of astrocytes as assessed by glial fibrillary acidic protein of more than 95% purity.

cDNA arrays were probed with cDNA synthesized from the isolated astrocyte samples and signals with >3-fold change are listed in Table 2. As noted, in some cases the changes are greater than 10-fold.

TABLE 2

Isolated Astrocytes
(Increased or decreased by >2.5 fold versus normal astrocyte in arrays)

| Gene Name | Mouse ACCN | Fold Change vs NL |
|---|---|---|
| CD24a | NM_009846 | 0.14964292 |
| Laminin | U59865 | 0.14964292 |
| EphA3.kinase neuon dev. | NM_010140 | 6.716634602 |
| ApoC1 | | 0.045251392 |
| ApoC2 | | 0.019825293 |
| ApoD | L39123 | 8.154290471 |
| IGFbp6 insulin binding | X81584 | 7.432680984 |
| TGFBbp2 | NM_013589 | 2.481789624 |
| lipocalin2 | NM_008491 | 0.043921834 |
| nephroblastoma overexpressing | NM_010930 | 18.22212847 |
| pentaxin related | NM_008987 | 7.958019291 |
| c-fos | NM_010234 | 3.197442844 |
| aquaporin | NM_007472 | 6.108595186 |
| osteoglycin | NM_008760 | 4.187526122 |
| perlecan | M77174 | 5.404873448 |
| collagen Ia1 | NM_000088 | 5.855510685 |
| collagen IIIa1 | X52046 | 7.022052515 |
| PDGFRb | NM_008809 | 2.811634865 |
| natriuretic peptide receptor | NM_008728 | 12.75206344 |
| NTR2 | NM_008747 | 0.025452654 |
| BMP4 | NM_007554 | 3.899393185 |
| BDNF | X55573 | 4.232877127 |
| Fibroblast inducible secreted | M70642 | 2.35671182 |
| angiopoietin2 | NM_007426 | 2.617360435 |
| PDE8 | AF067806 | 3.023374678 |
| AnnexinA1 | NM_010730 | 2.793346215 |
| RAbp1 (retionic acid bind protein) | NM_013496 | 4.941705445 |
| cathepsinK | X94444 | 3.140868488 |
| BP3 alloantigen | | nd |
| aryl hydrocarbon receptor | | nd |
| fibrinolysin | | nd |
| thrombospondin 2 | | nd |

B cells, T cells and myeloid cells were isolated from mock-inoculated and CJD-inoculated mice by MAC chromatography; B and T cell populations were 95% pure and myeloid cell populations were 80-85% pure.

Table 3 shows the levels of mRNA's (as determined from cDNA arrays) in B cells where differences more than 2.5-fold were found for at least 2 timepoints at 10 days, 30 days and 50 days after inoculation.

Similar results for myeloid cells are shown in Table 4.

TABLE 3

B Cell cDNA Expression Arrays for CJD versus normal Data Corroborated using two Normal B Cell Arrays and at least 2 different CJD time points

| GENE | GENBANK |
| --- | --- |
| selectin, lymphocyte | M25324 |
| apolipoprotein CII | Z15090 |
| ATP-binding cassette, sub-family A (ABC 1), member 1 | X75926 |
| Fc receptor, IgE, high affinity I, gamma polypeptide | J05020 |
| aminolevulinic acid synthase 2, erythroid | M63244 |
| tumor necrosis factor (ligand) superfamily, member 12 | AF030100 |
| cytotoxic granule-associated RNA-binding protein 1 | U00689 |
| fibroblast growth factor receptor 1 | X51893 |
| fibroblast growth factor receptor 4 | X59927 |
| FMS-like tyrosine kinase 4 | L07296 |
| glial cell line derived neurotrophic factor family receptor alpha 2 | AF002701 |
| 5-hydroxytryptamine (serotonin) receptor 2B | Z15119 |
| complement receptor 2 | M35684 |
| mitogen activated protein kinase kinase kinase 3 | U43187 |
| centrin 2 | D16301 |
| programmed cell death 6 | U49112 |
| cathepsin S | AJ223208 |
| keratin complex 1, acidic, gene 16 | AF053235 |
| DNA polymerase alpha 2, 68 kDa | D13546 |
| hippocampus abundant gene transcript 1 | D88315 |
| tumor necrosis factor, alpha-induced protein 1 (endothelial) | AF061346 |

TABLE 4

Myeloid Cell cDNA Expression Arrays CJD vs NI Genes of interest to define CJD infection peripherally from array studies

| GENE | GENBANK |
| --- | --- |
| CD82 antigen | D14883 |
| CD83 antigen | AF001041 |
| cAMP responsive element binding protein 3 | L22167 |
| macrophage migration inhibitory factor | Z23048 |
| pore forming protein | X60165 |
| aminolevulinic acid synthase 2, erythroid | M63244 |
| eukaryotic translation initiation factor 4E binding protein 2 | U75530 |
| tumor necrosis factor (ligand) superfamily, member 12 | AF030100 |
| chemokine (C-C) receptor 2 | U47035 |
| chemokine (C-X3-C) receptor 1 | AF074912 |
| tumor necrosis factor receptor superfamily, member 1b | M59378 |
| tumor necrosis factor receptor superfamily, member 1a | L26349 |
| interleukin 6 receptor, alpha | X53802 |
| cathepsin S | AJ223208 |

The invention claimed is:

1. A method to assess a likelihood that a subject has been infected with a transmissible spongiform encephalopathy (TSE) which method comprises:

determining, in a sample of brain tissue, cerebrospinal fluid or an isolated brain cell preparation taken from said subject before clinical signs of infection appear, the level of expression of the marker serum amyloid A3 (SAA3) in combination with the level of expression of at least two of the additional markers L-selectin, MIP-1α, CX3CR1 and ImmResG1, whereby an increase in the level of expression of each marker of the combination in said sample at least 2 fold as compared to the level in a corresponding control sample indicates the likelihood that the subject has been infected with TSE.

2. The method of claim 1 wherein the brain cell preparation is of the microglia.

3. The method of claim 1 wherein said additional marker includes L-selectin.

4. The method of claim 1 wherein said additional marker includes MIP-1α.

5. The method of claim 1 wherein said additional marker includes CX3CR1.

6. The method of claim 1 wherein said additional marker includes ImmResG1.

* * * * *

SEQUENCE LISTING

```
<160> NUMBER OF SEQ ID NOS: 48

<210> SEQ ID NO 1
<211> LENGTH: 21
<212> TYPE: DNA
<213> ORGANISM: Artificial Sequence
<220> FEATURE:
<223> OTHER INFORMATION: Primer

<400> SEQUENCE: 1
ggacagcggc ccccaaggac t                                      21

<210> SEQ ID NO 2
<211> LENGTH: 25
<212> TYPE: DNA
<213> ORGANISM: Artificial Sequence
<220> FEATURE:
<223> OTHER INFORMATION: Primer

<400> SEQUENCE: 2
caggccgagg ggaaaatgag gaatc                                  25

<210> SEQ ID NO 3
<211> LENGTH: 23
<212> TYPE: DNA
<213> ORGANISM: Artificial Sequence
<220> FEATURE:
<223> OTHER INFORMATION: Primer
```

```
<400> SEQUENCE: 3
ctacggggct acacagaaag tcg                                         23

<210> SEQ ID NO 4
<211> LENGTH: 27
<212> TYPE: DNA
<213> ORGANISM: Artificial Sequence
<220> FEATURE:
<223> OTHER INFORMATION: Primer

<400> SEQUENCE: 4
cagggaaaag cagaaagcca gtgaaga                                     27

<210> SEQ ID NO 5
<211> LENGTH: 21
<212> TYPE: DNA
<213> ORGANISM: Artificial Sequence
<220> FEATURE:
<223> OTHER INFORMATION: Primer

<400> SEQUENCE: 5
ggcaacccgg aggagaacta a                                           21

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
ccactgggag ggggtatgtc                                             20

<210> SEQ ID NO 7
<211> LENGTH: 22
<212> TYPE: DNA
<213> ORGANISM: Artificial Sequence
<220> FEATURE:
<223> OTHER INFORMATION: Primer

<400> SEQUENCE: 7
cagggccagt gcgggtcttg tt                                          22

<210> SEQ ID NO 8
<211> LENGTH: 30
<212> TYPE: DNA
<213> ORGANISM: Artificial Sequence
<220> FEATURE:
<223> OTHER INFORMATION: Primer

<400> SEQUENCE: 8
gttgtcccgg tctttggcta ttttgatgta                                  30

<210> SEQ ID NO 9
<211> LENGTH: 25
<212> TYPE: DNA
<213> ORGANISM: Artificial Sequence
<220> FEATURE:
<223> OTHER INFORMATION: Primer

<400> SEQUENCE: 9
cttcctcaga tccgaagcca gattg                                       25

<210> SEQ ID NO 10
<211> LENGTH: 22
```

```
<212> TYPE: DNA
<213> ORGANISM: Artificial Sequence
<220> FEATURE:
<223> OTHER INFORMATION: Primer

<400> SEQUENCE: 10
tcgcccaatt caggattgtc ag                                              22

<210> SEQ ID NO 11
<211> LENGTH: 24
<212> TYPE: DNA
<213> ORGANISM: Artificial Sequence
<220> FEATURE:
<223> OTHER INFORMATION: Primer

<400> SEQUENCE: 11
accaccggca gcaatgtaac cctg                                            24

<210> SEQ ID NO 12
<211> LENGTH: 26
<212> TYPE: DNA
<213> ORGANISM: Artificial Sequence
<220> FEATURE:
<223> OTHER INFORMATION: Primer

<400> SEQUENCE: 12
gtcgttcttg ctgcttacag gattgc                                          26

<210> SEQ ID NO 13
<211> LENGTH: 22
<212> TYPE: DNA
<213> ORGANISM: Artificial Sequence
<220> FEATURE:
<223> OTHER INFORMATION: Primer

<400> SEQUENCE: 13
caacaaaacc aaggtccagg ga                                              22

<210> SEQ ID NO 14
<211> LENGTH: 22
<212> TYPE: DNA
<213> ORGANISM: Artificial Sequence
<220> FEATURE:
<223> OTHER INFORMATION: Primer

<400> SEQUENCE: 14
ccaatgatga gaggcagcaa ga                                              22

<210> SEQ ID NO 15
<211> LENGTH: 21
<212> TYPE: DNA
<213> ORGANISM: Artificial Sequence
<220> FEATURE:
<223> OTHER INFORMATION: Primer

<400> SEQUENCE: 15
agctgctcag gacctcacca t                                               21

<210> SEQ ID NO 16
<211> LENGTH: 21
<212> TYPE: DNA
<213> ORGANISM: Artificial Sequence
<220> FEATURE:
<223> OTHER INFORMATION: Primer

<400> SEQUENCE: 16
```

-continued

```
gtcatatgca ggaactctgg g                                                21

<210> SEQ ID NO 17
<211> LENGTH: 27
<212> TYPE: DNA
<213> ORGANISM: Artificial Sequence
<220> FEATURE:
<223> OTHER INFORMATION: Primer

<400> SEQUENCE: 17
cagccatgtg gctggccatt ctgcttg                                          27

<210> SEQ ID NO 18
<211> LENGTH: 27
<212> TYPE: DNA
<213> ORGANISM: Artificial Sequence
<220> FEATURE:
<223> OTHER INFORMATION: Primer

<400> SEQUENCE: 18
acttcagagt agcaatatag agtccgc                                          27

<210> SEQ ID NO 19
<211> LENGTH: 23
<212> TYPE: DNA
<213> ORGANISM: Artificial Sequence
<220> FEATURE:
<223> OTHER INFORMATION: Primer

<400> SEQUENCE: 19
gacctcaact acatggtcta cat                                              23

<210> SEQ ID NO 20
<211> LENGTH: 23
<212> TYPE: DNA
<213> ORGANISM: Artificial Sequence
<220> FEATURE:
<223> OTHER INFORMATION: Primer

<400> SEQUENCE: 20
tggttcacac ccatcacaaa cat                                              23

<210> SEQ ID NO 21
<211> LENGTH: 24
<212> TYPE: DNA
<213> ORGANISM: Artificial Sequence
<220> FEATURE:
<223> OTHER INFORMATION: Primer

<400> SEQUENCE: 21
tgcaagtgtc tgaagcagct atgg                                             24

<210> SEQ ID NO 22
<211> LENGTH: 25
<212> TYPE: DNA
<213> ORGANISM: Artificial Sequence
<220> FEATURE:
<223> OTHER INFORMATION: Primer

<400> SEQUENCE: 22
ggtgggtgtg ccgtctttca ttaca                                            25

<210> SEQ ID NO 23
<211> LENGTH: 23
<212> TYPE: DNA
<213> ORGANISM: Artificial Sequence
```

```
<220> FEATURE:
<223> OTHER INFORMATION: Primer

<400> SEQUENCE: 23
actctgggaa atggaacgat gac                                           23

<210> SEQ ID NO 24
<211> LENGTH: 24
<212> TYPE: DNA
<213> ORGANISM: Artificial Sequence
<220> FEATURE:
<223> OTHER INFORMATION: Primer

<400> SEQUENCE: 24
aatgaagagg gggttgtagt cacc                                          24

<210> SEQ ID NO 25
<211> LENGTH: 28
<212> TYPE: DNA
<213> ORGANISM: Artificial Sequence
<220> FEATURE:
<223> OTHER INFORMATION: Primer

<400> SEQUENCE: 25
tatcctgctg ctggcccttaa tggtgtcc                                     28

<210> SEQ ID NO 26
<211> LENGTH: 28
<212> TYPE: DNA
<213> ORGANISM: Artificial Sequence
<220> FEATURE:
<223> OTHER INFORMATION: Primer

<400> SEQUENCE: 26
cgtggttagc gctggtgagg gttatgtc                                      28

<210> SEQ ID NO 27
<211> LENGTH: 24
<212> TYPE: DNA
<213> ORGANISM: Artificial Sequence
<220> FEATURE:
<223> OTHER INFORMATION: Primer

<400> SEQUENCE: 27
ccactcacct gctgctactc attc                                          24

<210> SEQ ID NO 28
<211> LENGTH: 25
<212> TYPE: DNA
<213> ORGANISM: Artificial Sequence
<220> FEATURE:
<223> OTHER INFORMATION: Primer

<400> SEQUENCE: 28
gtcactccta cagaagtgct tgagg                                         25

<210> SEQ ID NO 29
<211> LENGTH: 22
<212> TYPE: DNA
<213> ORGANISM: Artificial Sequence
<220> FEATURE:
<223> OTHER INFORMATION: Primer

<400> SEQUENCE: 29
gaagagtccc tcgatgtggc ta                                            22
```

<210> SEQ ID NO 30
<211> LENGTH: 23
<212> TYPE: DNA
<213> ORGANISM: Artificial Sequence
<220> FEATURE:
<223> OTHER INFORMATION: Primer

<400> SEQUENCE: 30 ccctttctg ttctgctgac aag                                             23

<210> SEQ ID NO 31
<211> LENGTH: 24
<212> TYPE: DNA
<213> ORGANISM: Artificial Sequence
<220> FEATURE:
<223> OTHER INFORMATION: Primer

<400> SEQUENCE: 31
ccacaatagc agagaaacag caat                                            24

<210> SEQ ID NO 32
<211> LENGTH: 22
<212> TYPE: DNA
<213> ORGANISM: Artificial Sequence
<220> FEATURE:
<223> OTHER INFORMATION: Primer

<400> SEQUENCE: 32
aaccccgagc aacaccatga ag                                              22

<210> SEQ ID NO 33
<211> LENGTH: 26
<212> TYPE: DNA
<213> ORGANISM: Artificial Sequence
<220> FEATURE:
<223> OTHER INFORMATION: Primer

<400> SEQUENCE: 33
agagacatca gggtagaaga ctgctg                                          26

<210> SEQ ID NO 34
<211> LENGTH: 25
<212> TYPE: DNA
<213> ORGANISM: Artificial Sequence
<220> FEATURE:
<223> OTHER INFORMATION: Primer

<400> SEQUENCE: 34
ataggctggt cctgagcagg gtttc                                           25

<210> SEQ ID NO 35
<211> LENGTH: 25
<212> TYPE: DNA
<213> ORGANISM: Artificial Sequence
<220> FEATURE:
<223> OTHER INFORMATION: Primer

<400> SEQUENCE: 35
atgaagcctt ccattgccat cattc                                           25

<210> SEQ ID NO 36
<211> LENGTH: 24
<212> TYPE: DNA
<213> ORGANISM: Artificial Sequence
<220> FEATURE:
<223> OTHER INFORMATION: Primer

<400> SEQUENCE: 36
tcagtatctt ttaggcaggc cagc                                    24

<210> SEQ ID NO 37
<211> LENGTH: 25
<212> TYPE: DNA
<213> ORGANISM: Artificial Sequence
<220> FEATURE:
<223> OTHER INFORMATION: Primer

<400> SEQUENCE: 37
acagtagaga acagcaaggt cttcc                                   25

<210> SEQ ID NO 38
<211> LENGTH: 23
<212> TYPE: DNA
<213> ORGANISM: Artificial Sequence
<220> FEATURE:
<223> OTHER INFORMATION: Primer

<400> SEQUENCE: 38
gctcttgcag ccgaggcaag aac                                     23

<210> SEQ ID NO 39
<211> LENGTH: 24
<212> TYPE: DNA
<213> ORGANISM: Artificial Sequence
<220> FEATURE:
<223> OTHER INFORMATION: Primer

<400> SEQUENCE: 39
gcagtttcca actctggatc tacc                                    24

<210> SEQ ID NO 40
<211> LENGTH: 27
<212> TYPE: DNA
<213> ORGANISM: Artificial Sequence
<220> FEATURE:
<223> OTHER INFORMATION: Primer

<400> SEQUENCE: 40
gtgtttgcaa agacatttga aagggtg                                 27

<210> SEQ ID NO 41
<211> LENGTH: 25
<212> TYPE: DNA
<213> ORGANISM: Artificial Sequence
<220> FEATURE:
<223> OTHER INFORMATION: Primer

<400> SEQUENCE: 41
tcgttcagtg agctaccaca gttgc                                   25

<210> SEQ ID NO 42
<211> LENGTH: 24
<212> TYPE: DNA
<213> ORGANISM: Artificial Sequence
<220> FEATURE:
<223> OTHER INFORMATION: Primer

<400> SEQUENCE: 42
tgccattagg cagggtgcca ttgg                                    24

<210> SEQ ID NO 43

```
<211> LENGTH: 25
<212> TYPE: DNA
<213> ORGANISM: Artificial Sequence
<220> FEATURE:
<223> OTHER INFORMATION: Primer

<400> SEQUENCE: 43
tttctcttgg ttaggccaac tcagg                                          25

<210> SEQ ID NO 44
<211> LENGTH: 25
<212> TYPE: DNA
<213> ORGANISM: Artificial Sequence
<220> FEATURE:
<223> OTHER INFORMATION: Primer

<400> SEQUENCE: 44
actgggattt catctaagcc gttgg                                          25

<210> SEQ ID NO 45
<211> LENGTH: 22
<212> TYPE: DNA
<213> ORGANISM: Artificial Sequence
<220> FEATURE:
<223> OTHER INFORMATION: Primer

<400> SEQUENCE: 45
gctggaagac tcctcccagg ta                                             22

<210> SEQ ID NO 46
<211> LENGTH: 21
<212> TYPE: DNA
<213> ORGANISM: Artificial Sequence
<220> FEATURE:
<223> OTHER INFORMATION: Primer

<400> SEQUENCE: 46
atgatccgcg acgtggaact g                                              21

<210> SEQ ID NO 47
<211> LENGTH: 20
<212> TYPE: DNA
<213> ORGANISM: Artificial Sequence
<220> FEATURE:
<223> OTHER INFORMATION: Primer

<400> SEQUENCE: 47
tccatgacgt tcctgatgct                                                20

<210> SEQ ID NO 48
<211> LENGTH: 20
<212> TYPE: DNA
<213> ORGANISM: Artificial Sequence
<220> FEATURE:
<223> OTHER INFORMATION: Primer

<400> SEQUENCE: 48
tccatgagct tcctgatgct                                                20
```